United States Patent
Gullick

[11] Patent Number: 5,494,638
[45] Date of Patent: Feb. 27, 1996

[54] SUPPORT MEMBRANE

[75] Inventor: Stephen P. Gullick, Ipswich, England

[73] Assignee: Hypoguard (UK) Limited, Suffolk, England

[21] Appl. No.: 311,713

[22] Filed: Sep. 23, 1994

Related U.S. Application Data

[63] Continuation of Ser. No. 832,894, Feb. 10, 1992, abandoned.

[30] Foreign Application Priority Data

Jun. 19, 1991 [GB] United Kingdom .................. 9113211

[51] Int. Cl.$^6$ .................................................. G01N 21/17
[52] U.S. Cl. .................. 422/56; 422/58; 435/805; 436/170
[58] Field of Search ....................... 422/56–58, 61; 435/805; 436/170

[56] References Cited

U.S. PATENT DOCUMENTS

| | | |
|---|---|---|
| 4,824,639 | 4/1989 | Hildenbrand et al. .............. 422/57 |
| 4,935,346 | 6/1990 | Phillips et al. .................. 435/435 |
| 5,019,347 | 5/1991 | Hiratsuka et al. ................ 422/56 |
| 5,049,487 | 9/1991 | Phillips et al. .................. 435/435 |
| 5,059,394 | 10/1991 | Phillips et al. ................. 422/435 |
| 5,160,436 | 11/1992 | Hildenbrand et al. ............. 422/56 |

*Primary Examiner*—Lyle A. Alexander
*Attorney, Agent, or Firm*—Nixon & Vanderhye

[57] ABSTRACT

The present invention relates to a membrane suitable for use as the support for one or more test reagents for testing a material applied to the membrane, which membrane is characterized in that it is initially an open pored porous material and in that at least part of the length the pores therein are blinded so that cell wall fragments from the material applied to the membrane are substantially prevented from passage through the membrane. Preferably, the pores are totally blinded by a gelatin matix containing one or more reagents which react with a fluid applied to one surface of the membrane to give a color which can be observed from a second surface of the membrane.

7 Claims, 1 Drawing Sheet

SUPPORT MEMBRANE

This is a Rule 62 Continuation of application Ser. No. 07/832,894, filed 10 Feb. 1992, now abandoned.

The present invention relates to a support medium, notably to a support medium for a blood analysis reagent.

BACKGROUND TO THE INVENTION

Typically, the analysis or testing of blood for the presence of glucose or other materials is carried out by applying a droplet of the blood to a test strip which carries a pad of a mixture of reagents which give a colour indication in response to one or more of the materials under test. The test strip typically carries the reagent(s) in a gelatin or other inert polymer or gel matrix pad at one end of a white plastic strip. However, this method suffers from the problems of contamination both of the sample by airborne and other materials and from the risk of cross-contamination of the samples on the tests sticks where an operator is handling a number of tests simultaneously. It is also necessary to remove excess blood sample to enable the colour developing in the reagent pad to be observed, and this may lead to rupture or smearing of the reagent pad. There is also the problem of disposing of the bloodied test stick after the test has been completed.

It has been proposed, in for example U.S. Pat. No. 4,935,346, to apply the blood sample to one side of a translucent porous membrane carrying a reagent mixture within the pores so that the plasma of the blood flows into the pores and reacts with the reagent to develop a colour which is then observed from the other side of the membrane as it develops. Such a technique will be denoted hereinafter as a back reading technique.

However, we have found that if the pores are of a size which can be readily achieved with conventional manufacturing techniques, the surface tension effects at the entry to each pore passage are so great that the wall of a blood cell in contact with the face of the membrane is ruptured and the colour visible from the other face of the membrane is distorted by the presence of red cell wall fragments which have penetrated into the pores. It is therefore necessary to take extra colour readings to compensate for this distortion, which adds to the complexity of the process and the cost of devices for use therein.

It has been proposed to apply a surface coating to the membrane, including the internal walls of the pores thereof, so as to increase the cell protein binding properties of the membrane material. However, this treatment does not overcome the cell wall rupture problems described above and fragments of the cell wall still pass through the membrane to affect the colour observed.

We have now devised a means by which this problem can be reduced and by which a membrane suitable for use in the back reading technique can be produced which does not cause significant rupture of the blood cell walls. In our invention the pores which are intially present in the membrane are blocked or blinded so that there is no free flow of fluid into the pores and the fluid component to be tested is separated from cellular components of a material to be tested by the membrane. In this way, the membrane can be mounted as an end wall of a chamber into which the blood is introduced for testing. The sample of blood is thus held enclosed within the chamber and the risk of external contamination and cross-contamination from other samples is reduced. Also, since the sample is retained within the chamber, the problems associated with disposal of the sample after testing are reduced.

SUMMARY OF THE INVENTION

Accordingly, the present invention provides a membrane suitable for use as the support for one or more test reagents for testing a material applied to the membrane, and particularly for use in a back reading technique in which blood plasma is separated from blood cells in a sample of blood applied to one surface of the membrane and the response of a reagent carried by the membrane is observed from another surface of the membrane, which membrane is characterised in that initially it is an open pored porous material and in that at least part of the length the pores therein are blinded so that cell wall fragments are substantially prevented from passage through the membrane. Preferably, substantially the whole length of the bores of the pores are blinded and the blinding agent either substantially completely fills the cross-section of the bores or the bores are blocked to the extent that the effective pore size of the membrane is reduced to a size below that at which rupture of the cell wall in the cellular component of the material applied to the membrane occurs to any significant extent.

Preferably, the membrane is a porous plastic sheet material, although other forms of membrane, for example a tube or other shaped member formed from or carrying the membrane can be used in desired. Thus, the membrane can be in the form of a conventional blood test stick. However, as stated above, the invention is of especial application in a back read test device, notably one in which the membrane forms one wall of a container for the fluid sample, so that the sample is held within the container and is isolated from the environment once it has been fed into the container.

The membrane forms a means for separating the non-cellular fluid from any cellular components of the fluid to be tested which allows the non-cellular fluid to pass into the material blinding the pores of the membrane with reduced cell wall rupture. For convenience, the invention will be described hereinafter in terms of this preferred application.

The membrane can be made from a wide range of materials having regard to the fluid to be applied to it, the size and nature of the cellular components therein and the test which is to be carried out on the non-cellular fluid component. Typically, the membrane will be a sheet of open pored porous plastic, notably one with an initial pore size which is smaller than the size of the cells which it is desired to separate out from the fluid. However, this need not be the case, since the blinding of the pores will reduce the effective pore size to substantially zero. It will be preferred for most uses that the membrane have an initial pore size in the range 0.1 to 10, notably less than 1, micrometers. The membrane may be made from a wide range of polymeric materials, for example cellulose, nitrocellulose and other cellulose derivatives such as cellulose esters; spun or woven polyamide fibres; polyvinylidene polymers; polycarbonate polymers; polysulfone polymers; polyalkylene polymers; acrylic or methacrylic acid polymers or co-polymers; polyamide polymers; polytetrafluorethylene polymers and the like. The polymer will typically be in sheet form, but it may contain fibrous or other reinforcement if desired; or may be in the form of fine weave aperture woven fabrics. Such sheet materials will usually be flexible and will require mounting on a support member or the like for use. However, it is within the scope of the present invention to use a membrane in a rigid form, for example a sintered frit or ceramic having tortuous interconnecting interstices therethrough forming the pores which are to be blinded according to the invention. For convenience, the invention will be described hereinafter in terms of a sheet polymer as the membrane.

The pores can be formed within the membrane during its manufacture, as when a volatile material or a soluble salt or other material is incorporated into the polymers sheet, for example during calendaring thereof, and this is subsequently evaporated or leached out of the polymer to leave a series of interconnecting passages or pores. Alternatively, the pores can be formed after manufacture of the sheet polymer, for example by needling or spark eroding the sheet polymer. Typically, the pores in the membrane will have a mean diameter of from 0.1 to 10 micrometers, preferably from 0.1 to 1 micrometers and the membrane will have an air permeability of from 1.5 to 4 liters per minute per square centimeter at an applied pressure of 10 psig across the plane of the membrane. Many forms of such membrane materials are available commercially and may be used in their commercially available form.

The membrane is preferably sufficiently thick that the colour of any blood cells retained on the face to which the sample has been applied does not adversely affect the colour observed in the reagent with which the non-cellular components have interacted. Thus, the membrane can be a self supporting member, as with a blood test stick, or can be a thin membrane which is supported in a rigid structure, such as the container for the back reading technique. Typically, the membrane will be from 50 to 500 micrometers thick so that excessive amounts of sample are not bound into the blinding material in the pore volume of the membrane.

The pores of the membrane are at least partially blinded by a material so that the initial pore size is reduced to a level at which either the surface tension effect at the entry to the pores is reduced to below that at which rupture of the cell wall occurs and/or the pore is completely blocked by the blinding medium and thus does not cause rupture of the cells or does not allow the passage of significant amounts of cell wall fragments. Thus, the membrane can be padded in a fluid which carries solid particles suspended or dispersed therein or a colloidal solution of solid particles so that solid particles enter the pores and form a continuous mechanical blinding within the pores. In this case it may be desirable to apply a pre-coating to the pores to aid retention of the particles upon the walls of the pores. If desired, a thermoplastic or thermoset material can be used which is applied when molten, but which sets within the pores to form the blinding. The blinding is preferably carried out so as to blind the whole plan area of the membrane. However, it may be desired to provide the blinding to only a selected area of the membrane to which the blood or other material to be tested is applied. Alternatively, the membrane can be cut into discs or strips to provide the desired area of treated membrane.

Typically, the material used to blind the bores of the pores is a material which readily wets the walls of the pores so as to reduce the formation of air pockets within the membrane; is a material which is inert to the reagents and the fluid to be tested; and preferably acts as a carrier for the reagents to be used in the test so as to form a translucent matrix within the bore so that the colour developed within the bore of the pore can be observed.

It is also preferred that the material used to blind the pores form a solid or matrix plug within the bore of the pores rather than a plug of solid particles with fine interconnecting interstices throughout the plug. Thus, a fluid composition can be applied to the membrane to form a gel or solid matrix within the bores of the pores. In a particularly preferred embodiment, an aqueous solution or colloidal suspension of gelatin is used to form a gel plug within all or part of the length of the pore bores. The gelatin for present use preferably has a low or medium molecular weight, for example with an average molecular weight within the range 2,000 to 50,000. Such forms of gelatin are commercially available and may be used in their commercially avaiable forms. If desired, the commercial material can be subjected to a pre-treatment, for example acid washing or other conventional treatment, to render it suitable for use in blood analysis or testing.

The blinding of the pores can be carried out so that the whole length of each bore is blinded. However, this is often not necessary and blinding of only part of the length of the pore bores may give satisfactory results. The amount of blinding agent applied to a membrane will depend upon the pore diameter, the thickness of the membrane, the material to be tested and the nature of the test to be carried out. The optimum amount can readily be established by simple trial and error tests for any given case. However, where a gelatin blinding agent is used, we have found that the application of from 1 to 10, eg. 2 to 6, milligrams of gelatin per square meter of a 0.1 to 0.5 mm thick membrane will usually be required.

The blinding material can be applied to the membrane by any suitable method. For example, a solution or suspension of the material can be applied by spraying dipping, roller coating or padding to the membrane so as to load the membrane with the desired amount of blinding material. In the case of gelatin, the concentration of the gelatin in the total blinding mixture applied to the membrane can vary from about 400 parts by weight per 600 parts by volume of water or other carrier fluid for a gelatin having an average molecular weight of 2–3,000, to 100 parts by weight per 600 parts by volume of the carrier fluid for a gelatin having an average molecular weight in the range 25,000 to 40,000. The material can be assisted into the bores of the pores by applying suction to one face of the membrane to draw material into the pores and/or by applying a hydrostatic head to the membrane to force the blinding material into the pores.

The blinding agent may be one which sets in situ within the pores due to loss of water or due to a change in the rheological properties of the material, for example as when a fluid gels or a thixotropic material re-solidifies. Alternatively, the blinding material can be caused to set by a chemical change, as when a pre-polymer or monomer is caused to polymerise in situ. Where the blinding material does not set to a solid and/or might otherwise be susceptible to loss from the pores during storage and transit, it may be desirable to apply a sealing coating of a polymer or wax to the membrane which is removed prior to use.

The blinding agent will often act as the medium through which the products of the interaction of the material under assessment with one or more of the reagents in the matrix diffuse to interact with other components, for example a chromogen. It is therefore preferred that the blinding of the pores form a continuous body within the pore so that this diffusion may take place. This is particularly important where interaction between the fluid being assessed and an enzyme reagent takes place to release a product, for example hydrogen peroxide, which then reacts with another component, for example the chromogen o-tolidine to give a colour which is observed from the exposed outer face of the membrane.

As indicated above, the membranes of the invention find especial use to support reagents for some test to be carried out on a fluid applied to the membrane. For example, the membrane can support a surface coating of the reagents on that face opposed to the one to which the sample is applied so that the non-cellular fluid from the sample penetrates through the blinded pores and contacts the reagent layer. However, it is preferred that the reagents be incorporated in the blinding within the pores, for example by incorporating the appropriate reagents in an aqueous gel applied to the membrane, so that the non-cellular fluid interacts with the reagents in the pores of the membrane to provide a colouration to the blinding which can be observed from the other face of the membrane.

The membranes of the invention can be used in a wide range of applications where it is desired to separate the non-cellular fluid from the cellular components of a fluid for testing. Thus, the membranes can be used in the assessment of plant cellular materials and the like. However, the invention is of especial application in testing blood or other bodily fluids, notably for the glucose, urea or cholesterol content thereof.

DESCRIPTION OF THE DRAWINGS

The invention will now be described by way of illustration with respect to a preferred form thereof as shown in the accompanying drawings in which.

DESCRIPTION OF THE PREFERRED EMBODIMENT

Figure 1:
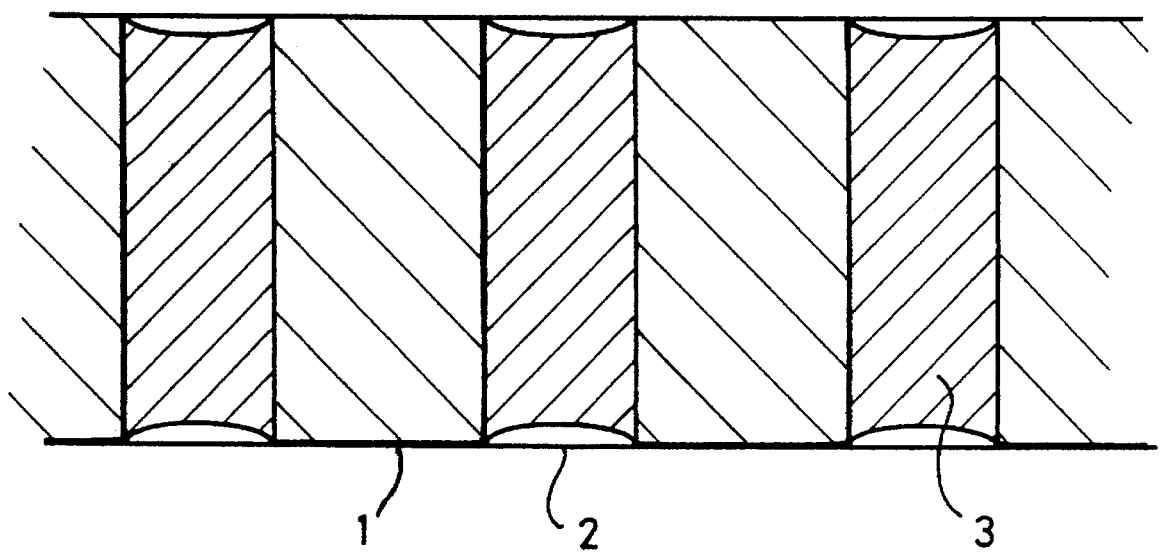
FIG. 1 is a diagrammatic sectional view through a membrane of the invention.
Figure 2:
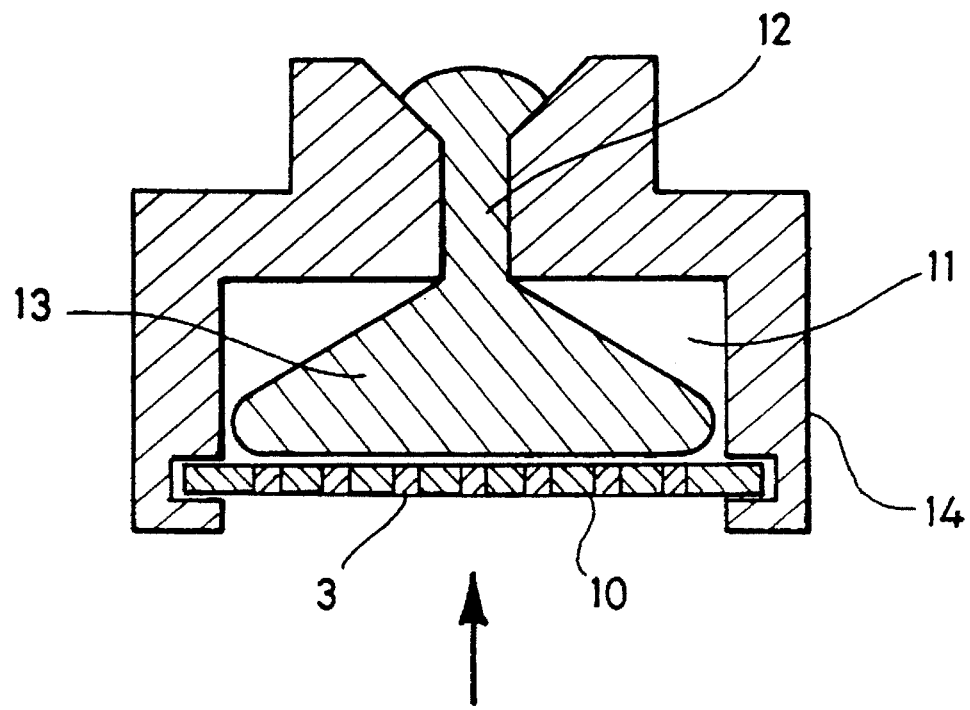
FIG. 2 shows the membrane is use in a back reading technique testing device.

A first solution was made by stirring together at room temperature 300 mls of de-ionised water, 200 mls of 0.5 Molar sodium phosphate buffer to give a pH of 7, 100 mls of a 20% w/v solution of the surfactant Gantrez and 300 gs of dry powdered gelatin having a molecular weight in the range 25,000 to 40,000.

A second solution was prepared by stirring together at 60° C. for one hour 300 mls of de-ionised water, 300 mls of methoxyethanol and 15 gs of o-tolidine hydrochloride or dianisidine hydrochloride.

The second solution was mixed dropwise with stirring into the first solution and the mixture stood for 1 hour at 60° C.

A third solution was made up by mixing 500,000 IUs of glucose oxidase and 30,000 IUs of peroxidase in 0.1 Molar solution of the sodium phosphate buffer. This solution was mixed with stirring into the other mixed solutions and filtered through a 0.1 micrometer aperture filter.

The resultant solution was impregnated into a polysulfone resin sheet 1 (0.2 to 0.4 mms thick and having a pore diameter of 0.2 micrometers and an air permeability of 3 liters per minute per square centimeter at an applied pressure of 10 psig) to provide 5 IUs of glucose oxidase, 3 IUs of peroxidase, 0.2 milligrams of o-tolidine and 4 milligrams of gelatin per square centimeter of the membrane 1. The impregantion was carried out by padding the membrane sheet through the aqueous solution. Since the polysulfone resin is hydrophylic, the gelatin solution wets the internal surfaces of the pores and the capillary action of the pores readily ensures that the gelatin solution enters the pores.

The padding is carried out first with the membrane one way up until the solution wets the upper surface of the membrane, then the other way up so that the pores 2 are substantially filled with the gelatin solution. The loaded membrane is allowed to dry so that a solid plug 3 of the gelatin gel is formed within the pores.

The membrane is cut into discs 10 which are used to form the end wall of a test chamber 11 having an open top or bore 12 into which a drop of blood 13 can be fed. The blood enters the chamber 11 so that it is held wholly within the test device 14. The blood 13 wets the inner face of the membrane and the non-cellular plasma penetrates the pores 2 by absorption or solution in the gelatin plug 3. The blood cells are prevented from entering the pores by the gelatin plug and little or no rupture of the blood cells occurs.

As the plasma diffuses through the gelatin matrix blinding the pores, it interacts with the reagents and gives a colour change which can be observed from the outer face of the device, as shown by the arrow. In this way the blood sample is not exposed to contamination and the test device can be disposed of without the risk of infection from the blood contained therein.

The membrane of the invention reduces the rupture of the blood cells and thus reduces the colouration observation errors due to blood cell fragments.

From a preferred aspect, the present invention thus provides a method for testing blood, which method comprises applying a sample of the blood to a first surface of an initially porous membrane, which membrane carries a gelatin based matrix containing at least one reagent to respond to a component in the blood therein, the said matrix substantially completely blinding the pores in the membrane in the area to which the said sample is applied, whereby red blood cells in the said sample are retained substantially unruptured at said first surface and the plasma of the said sample passes into the said matrix to interact with said reagent to produce a colour; and observing the colour from a second surface of said membrane.

The invention also provides a method for producing a membrane of the invention, which method comprises applying a fluid composition containing a blinding material to an initially porous membrane whereby the fluid penetrates the bores of the pores of the membrane; and allowing the composition to solidify so as to form a solid within the said pores which substantially completely occupies at least part of the length of the bores of the pores.

I claim:

1. A membrane suitable for use as a support for at least one test reagent for testing a fluid material containing cellular components which is to be applied to the membrane, which membrane is initially an open pored porous material and consists essentially of bores at least some of which have had at least part of their length blinded with a pore blinding material which is in a form selected from the group consisting of a solid, a gel and a matrix which substantially fills the transverse cross-section of said pores, whereby the said cellular components and fragments thereof in the material applied to the membrane are substantially prevented from entering the pores of the membrane and essentially no cell wall rupture occurs thereby reducing red coloration due to blood cell fragments.

2. A membrane as claimed in claim 1, wherein said transverse cross-section of the pores of the membrane are substantially completely filled for substantially all of their axial length with the blinding material.

3. A membrane as claimed in claim 1, wherein the bores of the pores of the membrane are blinded by a material containing at least one reagent which responds to a component in the material to be tested.

4. A membrane as claimed in claim 1, wherein the blinding material is a gelatin.

5. A membrane as claimed in claim 1, wherein the membrane is a polysulphone resin.

6. A fluid testing device incorporating a membrane as claimed in claim 1.

7. A device as claimed in claim 6, wherein the device comprises a sample retaining chamber for containing a sample of the fluid to be tested, said chamber having a wall thereof formed at least in part by said membrane which is to be contacted by a sample introduced into said chamber.

* * * * *

UNITED STATES PATENT AND TRADEMARK OFFICE
CERTIFICATE OF CORRECTION

PATENT NO. : 5,494,638
DATED : February 27, 1996
INVENTOR(S) : GULLICK

It is certified that error appears in the above-identified patent and that said letters patent is hereby corrected as shown below:

Column 5, line 36, delete "25,000 to 40,000" and replace by --2,500 to 4,000--.

Column 5, line 45, delete "30,000" and replace by --300,000--.

Signed and Sealed this

Eleventh Day of March, 1997

Attest:

BRUCE LEHMAN

Attesting Officer

Commissioner of Patents and Trademarks